United States Patent [19]

Butler et al.

[11] Patent Number: 4,538,017
[45] Date of Patent: Aug. 27, 1985

[54] CONVERSION OF PARAFFINS TO AROMATICS

[75] Inventors: James R. Butler; James M. Watson, both of Big Spring, Tex.

[73] Assignee: Cosden Technology, Inc., Dallas, Tex.

[21] Appl. No.: 636,852

[22] Filed: Aug. 1, 1984

[51] Int. Cl.³ .............................................. C07C 3/20
[52] U.S. Cl. .................... 585/415; 585/407; 585/330; 585/660; 208/134
[58] Field of Search ............... 585/415, 330, 417, 660, 585/661, 407

[56] References Cited

U.S. PATENT DOCUMENTS

| 3,756,942 | 9/1973 | Cattanach | 585/415 |
|---|---|---|---|
| 3,845,150 | 10/1974 | Yan et al. | 585/415 |
| 4,061,724 | 12/1977 | Grose et al. | 423/335 |
| 4,157,293 | 6/1979 | Plank et al. | 208/138 |
| 4,288,645 | 9/1981 | Wagstaff | 585/415 |
| 4,291,182 | 9/1981 | Dautzenberg et al. | 585/415 |
| 4,347,395 | 8/1982 | Chu et al. | 585/420 |
| 4,403,044 | 9/1983 | Post et al. | 518/714 |

OTHER PUBLICATIONS

Fyfe et al., Nature, vol. 296, pp. 530-533, (1982).
Fyfe et al., Chemistry Letters, (1983), pp. 1551-1554.
Thomas et al., Chemistry Letters, (1983), pp. 1554-1556.
Klinowski et al., Nature, vol. 296, pp. 553-536, (1982).
Wu et al., J. Phys. Chem., 83(21), 2777, (1979).
Olson et al., J. Catalysis, 61, 390-396, (1980).

Primary Examiner—D. E. Gantz
Assistant Examiner—A. Pal
Attorney, Agent, or Firm—William D. Jackson; John K. Abokhair

[57] ABSTRACT

A process for producing aromatic compounds from a paraffin containing feedstock in which the feedstock is passed to a reaction zone into contact with a multi-component catalyst system. The catalyst system comprises a discreet physical mixture of a silicalite homologation catalyst and a metal or metal oxide dehydrogenation catalyst. The process is carried out to cause the dehydrogenation of paraffins to olefins, the oligomerization of olefins to cyclic napthenes and the aromatization of the napthenes. Reaction conditions and relative catalyst concentrations to provide a relationship between the thermodynamic constraint for the dehydrogenation of the paraffins and the balancing of the kinetics of the dehydrogenation and oligomerization reactions to limit the olefin concentration to a value which does not result in substantial coking of the catalyst system.

21 Claims, 1 Drawing Figure

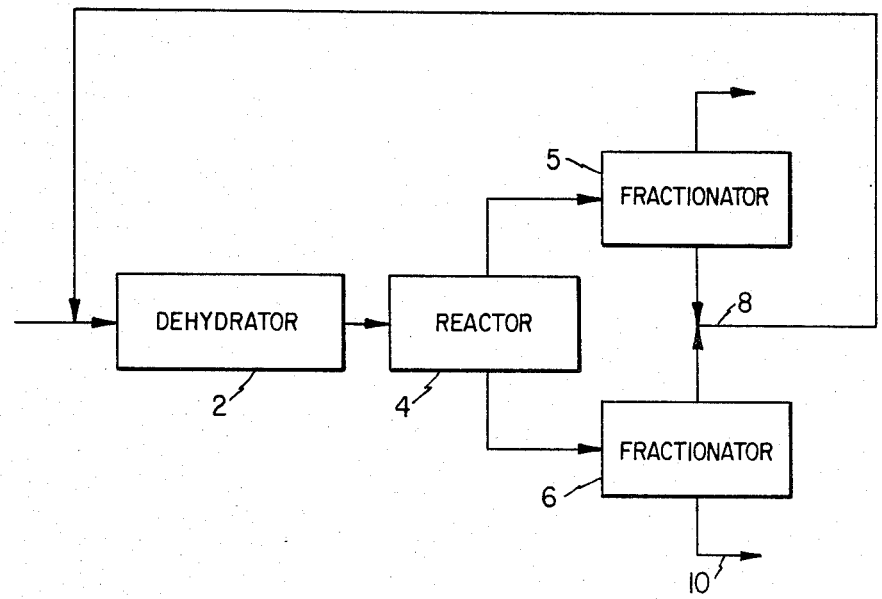

CONVERSION OF PARAFFINS TO AROMATICS

TECHNICAL FIELD

This invention relates to the aromatization of paraffinic feedstocks and more particularly to aromatization procedures employing catalyst systems of silicalite and dehydrogenation catalysts in which reaction thermodynamics and/or kinetics are adjusted to limit coke formation while providing an acceptably high conversion rate.

BACKGROUND ART

Various prior art processes involve the conversion of paraffinic hydrocarbons to aromatics. For example U.S. Pat. No. 4,347,395 to Chu et al discloses a process for producing aromatic compounds by contact of a gaseous hydrocarbon feedstock containing predominantly paraffinic hydrocarbons of two to six carbon atoms with oxygen or air in the presence of a catalyst system to convert at least a portion of the feed hydrocarbons to liquid aromatic hydrocarbons. The catalyst system comprises a crystalline zeolite catalyst in combination with a metal or metal oxide oxidative dehydrogenation component. Suitable dehydrogenation components include ferric oxide, potassium, oxide, and chromium oxide and a mixture of iron ferrite and an oxide of a metal selected from the group consisting of cerium zinc, manganese, lead and mixtures thereof. Other oxidative dehydrogenation components include a combination of the oxides of chromium, molybdenum and phosphorus or the oxides of niobium, vanadium and molybdenum. The zeolite and oxidative dehydrogenation component can be present in separate zones, in a single zone, or preferably a composite mixture of the two is prepared by ion exchange or at least partial impregnation of the dehydrogenation component into the zeolite material.

U.S. Pat. No. 4,288,645 to Wagstaff discloses the preparation of aromatic hydrocarbons and hydrogen from a lightweight hydrocarbon feed containing at least 50 weight percent propane. Conversion is effected at a temperature of 400°–700° C. and a pressure of between 5 and 10 bars in the presence of a crystalline silicate containing zinc as a promoter. The zinc is present in an amount within the range of 0.05–20 weight percent, preferably 0.1–5 weight percent, and may be incorporated into the silicate by ion exchange or by impregnation. U.S. Pat. No. 4,291,182 to Dautzenberg et al discloses a process similar to that found in the Wagstaff patent with the exception that the feed stream contains more than 50 weight percent butanes.

U.S. Pat. No. 4,403,044 to Post et al discloses a large number of conversion techniques including aromatization procedures employing feed streams selected from the class of carbon monoxide and hydrogen mixtures, acyclic organic compounds, aliphatic and/or cycloaliphatic hydrocarbons and mixtures thereof. A wide variety of silicalite based catalyst systems are disclosed for use in the conversion techniques of Post et al. The catalyst systems, based on silicalite as the carrier, include metal or metal combinations of nickel, copper, zinc, cadmium, platinum, palladium, nickel-tungsten, cobalt-molybdenum, nickel-molybdenum, zinc-palladium, zinc-copper, and zinc-rhenium. Other metal combinations include iron-chromium oxide, and zinc oxide-chromium oxide. Deposition of the metal combinations on the silicalite may be by impregnation.

DISCLOSURE OF THE INVENTION

In accordance with the present invention there is provided a new and improved process for the production of aromatic compounds from a paraffin containing feedstock. In carrying out the invention, the feedstock is passed into a reaction zone containing a catalyst system comprising a discrete physical mixture of a shape-selective crystalline silica polymorph silicalite homologation catalyst and a metal or metal oxide dehydrogenation catalyst. Within the reaction zone, the feedstock is passed into contact with the catalyst system at a temperature sufficient to cause the dehydrogenation of paraffinic hydrocarbons to olefins, the oligomerization of the olefinic hydrocarbons to cyclic naphthenes, and the aromatization of the naphthenes. The reaction zone temperature and pressure conditions and relative concentrations of the silicalite catalyst and the dehydrogenation catalyst are maintained so as to provide a relationship between the thermodynamic constraints for the dehydrogenation of the paraffinic hydrocarbons and the kinetics of the dehydrogenation and oligomerization reactions to limit the olefin concentration within the reaction zone to a desired value. This value is sufficiently low so that olefin concentration will not result in substantial coking of the catalyst system.

The olefin concentration may be limited through thermodynamic constraints, kinetic constraints, or a combination of both. Preferably, the rate constant for the oligomerization reaction is greater than the rate constant for the dehydrogenation reaction, thus limiting the olefin concentration to a value less than the equilibrium concentration at the pressure and temperature of the reaction zone. A preferred olefin concentration within reaction zone is 10 mole percent or less, based upon the paraffins in the feedstock. It is also preferred that the rate constant for the aromatization reaction be greater than the rate constant for the oligomerization reaction.

In a further aspect of the invention, gaseous and liquid effluents are withdrawn separately from the reaction zone and $C_3$–$C_5$ hydrocarbons are separated from the gaseous and liquid effluents and recycled to the reaction zone. In a preferred embodiment of the invention, the dehydrogenation catalyst is zinc oxide. The weight ratio of zinc oxide to silicalite normally is within the range of 0.1–1 and preferably within the range of 0.4–1. In another embodiment of the invention, the flow of paraffin containing feedstock to the reaction zone is interrupted and a nitrogenated air feed then supplied to the reaction zone to regenerate the catalyst system. During this regeneration step, the temperature of the reaction zone is maintained within the range of 400°–500° C.

BRIEF DESCRIPTION OF THE DRAWINGS

The drawing is a schematic flow diagram of an aromatization process carried out in accordance with the present invention.

BEST MODES FOR CARRYING OUT THE INVENTION

The present invention provides a process wherein substantially pure aromatic hydrocarbons are derived from paraffinic hydrocarbons by conversion over a catalyst system comprising a discrete physical mixture of a shape selective silicalite catalyst and a metal or metal oxide dehydrogenation catalyst. The paraffinic hydrocarbons in the feed stock may take the form of substituted or unsubstituted alkanes containing from 2 to about 16 carbon atoms. Preferably the feed stock is composed primarily of $C_3$–$C_5$ hydrocarbons without significant branching.

The conversion of paraffins to aromatic hydrocarbons may be expressed in terms of a three stage process involving dehydrogenation, oligomerization, and aromatization. While the reaction stages will be described as occurring sequentially, it will be recognized that all three reactions will take place simultaneously within the reaction zone. The first reaction stage involves the dehydrogenation of paraffins to form olefins. Olefins may be derived from paraffins by the direct dehydrogenation of a paraffin to form the corresponding olefin and hydrogen or by carbon-carbon fission to produce lower alkanes and olefins. At temperatures thermodynamically favoring dehydrogenation, i.e., temperatures of about 500°–700° C., the direct dehydrogenation reaction competes with carbon to carbon fission. At these temperatures and in the absence of a dehydrogenation catalyst, the predominant mechanism is fission of the carbon to carbon bond (C—C) which has a lower bond energy than the carbon-hydrogen bond (C—H). The higher the alkane, the greater the tendency toward carbon-carbon fission. Thus, in the case of ethane, the only reaction leading to olefin production is direct dehydrogenation. In the case of propane, two decomposition reactions are possible; one leading to propylene and free hydrogen the other to ethylene and methane, with the latter slightly predominating. In the case of butane, the predominant reaction is fission at the end of the carbon chain to produce propylene and methane with the next predominant reaction fission of the interior carbon atoms to produce ethane and ethylene. Only a minor amount of direct dehydrogenation resulting in butenes and free hydrogen takes place. As will be described in greater detail hereinafter, the present invention involves the use of a dehydrogenation catalyst which provides for a preferential acceleration of the dehydrogenation reactions relative to the carbon-carbon fission reaction.

In the second stage of the conversion process the olefins undergo oligomerization to produce cyclic naphthenes. These naphthenes are then dehydrogenated in the third stage of the conversion process to produce the corresponding aromatic compounds. The cyclic naphthenes include saturated cycloalkanes and unsaturated alicyclic compounds with the former usually predominating. The predominant cyclic naphthenes produced in the second stage are six member cyclic rings substituted with one or two alkyl groups containing a total of 1–12 carbon atoms. These cyclic naphthenes are dehydrogenated to produce the corresponding aromatic hydrocarbons e.g. benzene, toluene, ethylbenzene, xylenes and other alkyl toluenes.

As is recognized by those skilled in the art, a chemical reaction may be characterized thermodynamically by its equilibrium constant K, and kinetically by its rate constant k. The equilibrium constant is a measure of the product and reactant concentrations at equilibrium and the rate constant is a measure of the velocity at which the reaction takes place. The equilibriums of the reactions involved in the aforementioned conversion process may be controlled thermodynamically by varying the temperature and pressure. The rates at which the reactions proceed are functions of product and reactant concentrations, temperature, pressure and catalytic activities, as is understood by those skilled in the art. In summary, the thermodynamics of a chemical reaction determine the relative amount of a product formed by the reaction and the kinetics of the reaction determine the speed with which the product is formed. In the present invention, the chemical thermodynamics of the initial reaction stage and the kinetics of the successive reaction stages are balanced through the utilization of appropriate reaction conditions and catalysts to avoid excessive olefin accumulation within the reaction zone without unduly restricting the conversion of olefins to naphthenes and subsequent dehydrogenation to aromatics. For the sake of simplicity, the invention will be described in detail initially with reference to the conversion of propane to aromatic hydrocarbons. It will be understood, however, that the description immediately below is equally applicable to other paraffins and mixtures of paraffins.

The pyrolytic decomposition of propane to produce an olefin occurs in accordance with one of the two following reactions:

$$C_3H_8 \rightleftharpoons C_3H_6 + H_2 \tag{1}$$

$$C_3H_8 \rightarrow C_2H_4 + CH_4 \tag{2}$$

Reaction (1) is the less thermally favored reaction and at the temperatures involved is highly reversible while reaction (2) is essentially irreversible and has an equilibrium constant which is greater than the equilibrium constant for reaction (1) by several orders of magnitude. For example, at a temperature of 527° C. the equilibrium constants for reactions (1) and (2) are about 0.04 and 60, respectively. At this temperature, and a pressure of 6.9 bars, the equilibrium concentration of olefin produced by reaction (1) is 8 mole % as contrasted with 95 mole % for reaction (2).

The previously described reaction stages may be designated as successive reactions A, B, C and illustrated diagramatically as follows:

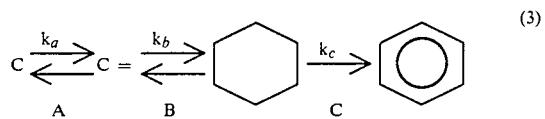
(3)

In relationship (3) paraffins are indicated by C, olefins by C=, naphthenes (cycloalkanes) by

and aromatics by

Reaction A represents the conversion of paraffins to olefins, reaction B the oligomerization of the olefins to form cyclic naphthenes, and reaction C the aromatization of the naphthenes through dehydrogenization. It will be recalled that the olefin conversion stage represented by reaction A occurs through direct dehydrogenization only in the case of ethane and, in the case of propane and the heavier paraffins, by direct dehydrogenization and carbon-carbon fission with the latter becoming proportionately greater as the molecular weight of the feed material increases. The rate constant for the production of olefins is indicated by $k_a$. The rate constant for oligomerization of the olefins to naphthenes is indicated by $k_b$, and the rate constant for reaction C, the dehydrogenization of the naphthenes to produce aromatics, is indicated by $k_c$. In relationship (3), reaction A is highly reversible under the conversion conditions in the presence of a dehydrogenation catalyst in accordance with the present invention. Under these conditions, reaction (B) is also highly reversible whereas reaction (C) is essentially irreversible.

The thermodynamic conversion parameters and the multicomponent catalyst systems employed in accordance with the present invention perform interrelated functions to provide a desired low olefin concentration within the reaction zone. Preferably, the olefinic reaction products (C= in relationship 3) are no greater than about 10 mole percent of the paraffinic hydrocarbons in the feedstream.

The multicomponent catalyst systems employed in the present invention provide dehydrogenation activities for reactions A and C and an oligomerization activity for reaction B. As described in greater detail hereinafter, catalytic activity for reactions A and C normally is provided by a single dehydrogenation catalyst although separate catalyst for each of reactions A and C may be employed if desired. The catalytic activity for reaction B is provided by a shape selective silicalite homologation catalyst. The silicalite is selective to the formation of cyclic compounds containing less than 12 carbon atoms with the large preponderance of cyclic hydrocarbons formed containing nine carbon atoms or less.

The presence of the hydrogenation catalyst enhances reaction (1) relative to reaction (2) as described above so that reaction (1) is the predominant mechanism for the production of olefins. The pressure and temperature conditions within the reaction zone may be controlled to thermodynamically limit the olefin concentration to the desired level. In this case, the rate constant $k_b$ may be the same as or even less than the rate constant for $k_a$. Preferably, however, the rate constant $k_b$ will be at least equal to the constant $k_a$ in order to avoid unduly limiting the overall conversion process. Alternatively, olefin concentration within the reaction zone may be limited kinetically. That is, the temperature and pressure conditions may be adjusted to values thermodynamically yielding an olefin concentration above the desired maximum amount, and the olefin concentration then maintained at a value below this equilibrium value by employing a rate constant $k_b$ which is sufficiently greater than the rate constant $k_a$ to prevent olefin concentration exceeding the desired limit. Usually it will be preferred to employ thermodynamic constraints either alone or in combination with kinetic limitation of olefin production.

The silicalite catalyst and the dehydrogenation catalyst preferably are employed in relative amounts so that the rate constant $k_b$ for the oligomerization of the olefins is equal to or greater than the rate constant $k_a$ but less than the rate constant $k_c$. It will be recalled that the temperature and pressure conditions in the reaction zone are adjusted to provide an equilibrium constraint which limits the amount of olefins thermodynamically obtainable. By maintaining a relatively small concentration of olefins within the reaction zone, coke formation is retarded and the activity of the silicalite catalyst is prolonged. The relatively low equilibrium constraint for reaction A will limit the overall rate of aromatization procedure if the reaction kinetics are not adjusted in accordance with the present invention. However by providing that the rate constant $k_b$ is equal to or greater than rate constant $k_a$, the olefinic products of reaction A are consumed as rapidly as they are formed. This minimizes the product concentration resulting from reaction A with the result that the reaction is constantly biased in the forward direction, thus removing the thermodynamic limitation on the overall conversion process. By providing that the rate constant for $k_c$ is greater than the rate constant $k_b$ the naphthenic hydrocarbons are aromatized as rapidly as they are formed by the homologation stage. This limits the decomposition of the naphthenic hydrocarbons to lighter products, thus enhancing the aromatic yield.

The catalyst systems employed in the present invention are discrete physical mixtures of a shape selective silicalite homologation catalyst and a metal or metal oxide dehydrogenation catalyst. By the term "dehydrogenation catalyst" is meant a catalyst which is highly selective to reaction (1) above. That is, the catalyst substantially accelerates reaction (1) relative to reaction (2) so that the proponderance of olefin production results from reaction (1). Suitable dehydrogenation catalyst include metal or metal compounds which include platinum, rhenium, zinc, iron, copper, gallium, antimony, tin, lead, bismuth, thallium, cadmium and chromium as described in greater detail hereinafter. Other suitable catalysts which preferentially accelerate the dehydrogenation reactions may be employed in carrying out the invention provided, of course, that they are compatible with the silicalite catalyst. The homologation catalyst is a crystalline silica material as contrasted with a zeolitic material which be definition is a silicate of aluminum and either sodium or calcium, or both, which demonstrates ion exchange capacity. These crystalline silica materials are silica polymorphs whose structures have been designated in the art as "silicalite." These materials, in contrast to aluminosilicate zeolites, demonstrate no appreciable ion exchange properties since $AlO_4$ tetrahedra do not comprise a portion of the crystalline silica framework. Aluminum may be present in these silicalite catalyst materials. However, its presence is a result of impurities in the silica source used to prepare the material and silicalite containing such alumina or other metal oxide impurities can in no sense be considered to be a metallo silicate. Further description and methods of preparing silicalite type catalyst are set forth in U.S. Pat. No. 4,061,724 to Grose, the entire disclosure of which is incorporated herein by reference.

The dehydrogenation catalyst and the silicalite catalyst may be mixed together in any suitable manner so long as the two catalyst retain their discrete physical characteristics in the final product. Thus the catalyst system may be in a particulate form comprising granules of the silicalite and granules of the dehydrogenation catalyst mixed together to provide the discrete physical mixture. The granular particles which normally will include the particular catalyst material in a binder matrix should be mixed thoroughly to provide a relatively homogeneous mixture. Alternatively, the catalyst system may be in a particulate form comprising pellets formed of mixtures of crystallites of the dehydrogenation catalyst and crystallites of the silicalite. Such pellets may be formed by any suitable technique, but typically will take the form of extrusion products. The extrudates may be formed by mixing crystallites of the dehydrogenation catalyst and the silicalite catalyst together with a binder material to form a plastic which is then extruded through a suitable die structure to form pellets of the desired size. Where pelletized mixed products formed by extrusion techniques are employed, the granular material typically will range in size from about 1-4 millimeters. Where mixtures of granular silicalite and granular dehydrogenation catalysts are used, the individual catalyst particles normally will range from about 0.2-2 millimeters.

Crystallites of the dehydrogenation catalyst may be mixed with crystallites of silicalite without binders in which case the size of the catalyst particular will be extremely small, on the order of 10 microns or less.

The use of a catalyst system comprising a physical admixture of discrete catalysts offers several important advantages over catalyst systems in which a metallic catalyst is impregnated into a silicalite base, as disclosed, for example, in the aforementioned patent to Post et al. The physical mixture permits the use of relatively large concentrations of metallic catalysts without plugging of the pore structure of the silicalite as would result from the use of too much metal in the impregnated catalyst form. Also, use of the particulate catalyst system will not be attended by wide swings in catalytic activity which may occur in the case of the metal impregnated catalyst as metal is lost from the pore structure. The advantages derived from the use of the particulate mixture over an impregnated catalyst system usually can be achieved without any increase in cost. In fact, in addition to providing greater constancy of performance, the particulate mixture will normally be simpler in formulation and lower in cost than the impregnated catalyst system.

A preferred dehydrogenation catalyst is zinc oxide. The zinc oxide may be in granular form and mixed with granules of silicalite catalyst in a particulate catalyst system. The dehydrogenation catalyst and the silicalite may be of any suitable particle size which can conveniently be mixed together and incorporated into the reaction vessel. In laboratory work relative to the invention particle sizes for each of the zinc oxides and silicalite catalysts of 40-60 and 10-20 mesh were employed. Alternatively, fine-grained crystallites of zinc oxide and silicalite catalyst may be mixed together with a binder to form pelletized products as described above. In laboratory work carried out relative to the invention, one-eighth inch extrudates (3.2 mm) formed from crystallites of zinc oxide and silicalite catalyst is an alumina binder where used. Smaller pellets e.g. one-sixteenth inch extrudates may also be employed.

Regardless of the form of the discrete physical mixture, the weight ratio of zinc oxide to silicalite normally will be within the range of about 0.1 to 1. It usually will be desirable to avoid employing zinc oxide in a ratio to silicalite of greater than 1 in order to keep coking of the silicalite to an acceptably low level. A zinc oxide to silicalite ratio of at least 0.1 usually should be used in order to provide sufficient dehydrogenation activity. For most feedstocks, the preferred zinc oxide/silicalite ratio in the multicomponent catalyst is within the range of 0.3 to 0.5.

The conversion conditions within the reaction zone necessary to thermodynamically limit olefin concentration while permitting the desired reaction kinetics in accordance with the invention, will vary somewhat depending upon the feedstream and the particular catalyst system employed. As will be understood by those skilled in the art, a reaction temperature of about 500° C. is necessary thermodynamically to cause the dehydrogenation reactions to proceed. An increase in temperature above this level will tend to drive both the direct dehydrogenation and the carbon-carbon fission reactions to the right while an increase in pressure will have a tendency to shift the reactions to the left albeit with a relatively small impact upon carbon-carbon fission. As noted previously the carbon-carbon fission reaction becomes progressively more favored than the direct dehydrogenation reaction as the average molecular weight of the paraffins in the feedstream increases.

For feedstocks containing paraffins predominantly within the $C_3$-$C_5$ range the conversion conditions normally will fall within a temperature range of about 500°-600° C. and a pressure range of about 2-21 bars.

In summary with respect to relationship (3) an increase in temperature within the reaction zone will tend to drive reactions A and C to the right and will tend to retard reaction B somewhat. Pressure will tend to have the reverse effect; i.e., an increase in pressure will tend to promote the oligomerization reaction but tend to promote the oligomerization reaction but retard the conversions to olefins and aromatics.

In experimental work relative to the invention, a number of different particulate catalyst systems were employed in tests involving the conversion of a propane feedstream to aromatic hydrocarbons. Tests were carried out employing a fixed bed reactor vessel containing in each instance equal parts of a silicalite catalyst and a dehydrogenation catalyst as described below. The tests were carried out under approximately the same conversion conditions. The inlet temperature to the reactor was approximately 520° C., the operating pressure of the reactor was about 20 bars and the weight hour space velocity (WHSV) of the feedstream over the catalyst was about 2. While conditions during the tests varied somewhat from the nominal parameters given immediately above, the variances were not considered to be experimentally significant.

The silicalite catalyst employed in the experimental work had a crystalline size of less than 8 microns and a ratio of silica to alumina in the tetrahedra molecular sieve network of at least about 200. This catalyst was mixed with equal parts of a second particulate catalyst. In test number 1, the second catalyst was a cobalt-molybdinum hydrodesulfurization catalyst (Shell HDS S-444).

In test number 2, the dehydrogenation catalyst was a composite platinum-rhenium catalyst (Engelhard 601) and in test number 3, the deyhdrogenation catalyst was zinc oxide (UCI G72D). In each case, 10-20 mesh particulate dehydrogenation catalyst and particulate silicalite catalyst were mixed to form the catalyst bed.

Test number 1 was carried out for a period of 33 hours, during the course of which the catalyst system displayed low activity and high susceptibility to coking. Very little of the feed was isolated as liquid. The aromatic products which were formed were highly alkylated with xylenes composing 35% of the liquid and $C_9+$ aromatics more than 40%.

Test number 2 was carried out for a period of 44 hours. During the first 24 hours the catalyst system retained fairly high activity. Thereafter propane conversion and liquid yield (including C5+ hydrocarbons collected in the gas effluent from the reactor) decreased significantly. The liquid yield of the total feed (including all C5+ hydrocarbons) was about 13 wt%. Propane conversion averaged about 56 wt% and selectivity to aromatics was about 16 wt%. Calculated selectivity assuming recycle of all products other than $H_2$, $CO$, $CO_2$, $CH_4$ and liquids was about 38 wt%. The presence of steam co-feed significantly decreased liquid formation.

The liquid product was composed of more than 95% aromatics. A representative analysis for the product is set forth in Table I.

The liquid product was composed of more than 95% aromatics. A representative analysis for the product is set forth in Table I.

TABLE I

| Component | Mole Percent |
| --- | --- |
| Non-aromatics | 4.5 |
| Benzene | 7.9 |
| Toluene | 31.5 |
| Ethylbenzene | 3.3 |
| p,m-xylene | 22.1 |
| o-xylene | 6.9 |
| $C_9$+ heavies | 23.8 |

Test no. 3 employing the zinc oxide dehydrogenation catalyst yielded the best results. The test was carried out for almost 6 days during which timer there was no evidence of excessive coke formation or loss of catalyst activity. The average liquid yield was about 15 weight percent of feed and about 20% of feed when the C5+ hydrocarbons in the gaseous effluent were included. Average propane conversion was about 61% with selectivity to aromatics of about 24% and calculated selectivity assuming recycled products as described above was about 55%. A representative composition of the liquid product is set forth in Table II.

TABLE II

| Component | Mole Percent |
| --- | --- |
| Non-Aromatics | 0.5 |
| Benzene | 13.6 |
| Toluene | 45.2 |
| Ethylbenzene | 1.6 |
| p-xylene | 6.5 |
| m-xylene | 12.5 |
| o-xylene | 5.8 |
| $C_9$+ heavies | 14.3 |

Representative analyses values for the feedstreams and gas effluents test runs 1, 2, and 3 are set forth in Table III.

TABLE III

| Comp | Test 1 Feed | Test 1 Effluent | Test 2 Feed | Test 2 Effluent | Test 3 Feed | Test 3 Effluent |
| --- | --- | --- | --- | --- | --- | --- |
| C5+ | 0.000 | 0.431 | 0.000 | 2.805 | 0.000 | 2.47 |
| H2 | 0.089 | 7.241 | 0.000 | 7.756 | 0.000 | 14.06 |
| C3 | 97.055 | 67.245 | 96.646 | 37.025 | 96.646 | 31.84 |
| C3= | 0.540 | 1.016 | 0.000 | 2.479 | 0.000 | 4.81 |
| IC4 | 0.736 | 1.253 | 0.187 | 2.392 | 0.187 | 1.02 |
| NC4 | 0.117 | 1.846 | 0.000 | 3.771 | 0.000 | 1.40 |
| C4=−1 | 0.000 | 0.056 | 0.000 | 0.186 | 0.000 | 0.05 |
| IC4= | 0.000 | 0.143 | 0.000 | 0.412 | 0.000 | 0.14 |
| TC4= | 0.000 | 0.076 | 0.000 | 0.225 | 0.000 | 0.07 |

TABLE III-continued

| Comp | Test 1 Feed | Test 1 Effluent | Test 2 Feed | Test 2 Effluent | Test 3 Feed | Test 3 Effluent |
| --- | --- | --- | --- | --- | --- | --- |
| CC4= | 0.000 | 0.054 | 0.000 | 0.165 | 0.000 | 0.05 |
| 1C5 | 0.000 | 0.168 | 0.000 | 0.347 | 0.000 | 0.18 |
| NC5 | 0.000 | 0.055 | 0.000 | 0.091 | 0.000 | 0.02 |
| C2= | 0.000 | 0.521 | 0.000 | 1.531 | 0.000 | 0.92 |
| C2 | 0.694 | 2.780 | 3.091 | 16.408 | 0.000 | 17.52 |
| CO2 | 0.009 | 1.083 | 0.000 | 0.032 | 3.091 | 0.21 |
| C1 | 0.020 | 4.583 | 0.000 | 23.523 | 0.000 | 25.11 |
| CO | 0.148 | 0.191 | 0.076 | 0.012 | 0.076 | 0.03 |
| H2S | 0.000 | 0.034 | 0.000 | 0.000 | 0.000 | 0.00 |

Additional experimental work was carried out employing the catalyst system as used in Test No. 3 with variations in the feedstream and the operating parameters. When the feed was converted from propane to ethane, substantially no conversion took place and the effluent gas contained about 80% ethane with hydrogen and methane as the other major components. When the feed was switched to butane, the composition of the liquid effluent was about the same as for propane but the yield increased about 5%. The selectivity to aromatics was also slightly higher than for propane.

An additional set of tests were carried out using the zinc oxide dehydrogenation catalyst identified earlier and 5 other metal catalysts. The results of this experimental work are summarized in Table IV. The catalysts used in this suite of experiments are referred in the table as catalysts A-F and are identified as follows: (A) zinc oxide (G-72D described earlier), (B) zinc oxide, (C) zinc oxide-copper oxide, (D) iron oxide dehydrogenation catalyst, (E) nickel methanation catalyst, and (F) copper chromite.

In Table IV, the bed temperature and pressure are give in columns 2 and 3, respectively. Column 4 identifies the metal catalyst by the code letters A-F as set forth above and column 5 gives the volume ratio of the metal catalyst to the homologation catalyst. Space velocities are given in columns 6 and 7 and the remaining columns set forth yield data as indicated. Column 9 gives the selectivity to aromatics based upon a single pass of feedstock through the reactor and column 10 gives the calculated selectivity assuming the recycle of products as described previously. The homologation catalyst was the silicalite described previously.

In test No. 11, the reaction chamber was packed with inert particulates and in run No. 12, the reaction chamber was empty. In the remaining runs, with the exceptions noted below, the catalyst systems were physical mixtures of particulate catalysts with each catalyst being within the range of 40-60 mesh. In run No. 16 the dehydrogenation catalyst and the silicalite were separate extrudates having nominal particle sizes of 3.2 mm and 1.6 mm respectively. In test No. 22, the catalyst system was formulated in unitary pellets of zinc oxide and silicalite crystallites which were mixed together with a binder and then extruded to form 3.2 mm pellets. The weight ratio of zinc oxide to silicalite in the extrudates was 1.0. In the experimental work depicted in Table IV, propane was employed as the feedstream except for test 14c. In this case the feedstream was ethane.

In this set of experiments, the catalysts A, B and C gave results which compared favorably to the results obtained in test No. 3 described previously. Catalyst D also produced favorable results but the activity of the catalyst decreased with time more rapidly than the zinc oxide containing catalysts. Catalyst F also deactivated at a relatively rapid rate and gave somewhat lower selectivities than the other dehydrogenation catalysts. The nickel methanation catalyst produced no measurable quality of aromatics.

TABLE IV

| EXP # | TEMP °C. | PRESS PSIG | CAT | RATIO | LHSV | WHSV | CONV OF C₃ % | WT. SEL TO AR. S PASS | WT SEL TO AR RECYCLE | WT SEL TO C₁ | WT SEL TO C₃= | WT SEL TO C₂ | NON AR CONTENT OF LIQ % | C₉+ CONT. OF LIQ | BZ CONT OF LIQ |
|---|---|---|---|---|---|---|---|---|---|---|---|---|---|---|---|
| 11 | 538 | 300 | Inerts | | 5 | 5 | 11.5 | 0 | 0 | 13.6 | 18.2 | 37.4 | 0 | 0 | 0 |
| 12 | 542 | 300 | None | | 5 | 5 | 17.2 | 0 | 0 | 18.1 | 21.6 | 24.4 | 0 | 0 | 0 |
| 13 | 534 | 290 | C | 0.1 | 4.65 | 3.04 | 75.5 | 21.1 | 24.0 | 23.1 | 1.3 | 42.9 | 1.6 | 16.8 | 11.7 |
| 14A | 527 | 295 | A | 0.1 | 4.65 | 3.24 | 75.6 | 22.8 | 24.3 | 24.4 | 1.2 | 45.3 | .9 | 18.4 | 11.8 |
| 14B | 516 | 305 | A | 0.1 | 9.30 | 6.49 | 60.3 | 14.1 | 17.6 | 20.4 | 3.6 | 43.6 | 2.3 | 14.9 | 8.5 |
| 14C | 558 | 300 | A | 0.1 | 11 | 3.6 | <1 | | 0 | | 0 | | | | |
| 15A | 470 | 51 | A | 0.5 | 11 | 6.51 | 5 | | | | | | | | |
| 15B | 495 | 51 | A | 0.5 | 11 | 6.51 | 15.7 | 5.52 | 12.6 | 8.5 | 12 | 22.4 | 1.9 | 5.6 | 7.9 |
| 15C | 508 | 51 | A | 0.5 | 11 | 6.51 | 17.6 | 26.7 | 43.3 | 7.4 | 11 | 19.7 | 1.8 | 12.3 | 9.9 |
| 15D | 502 | 51 | A | 0.5 | 2.28 | 1.34 | 34.7 | 35 | 47.2 | 6.3 | 3.8 | 32.5 | 1.1 | 13.4 | 14.7 |
| 15E | 500 | 300 | A | 0.5 | 2.28 | 1.34 | 62.8 | 24 | 26.4 | 21.8 | .6 | 43.5 | .8 | 19.4 | 9.8 |
| 16A | 504 | 70 | A | 0.5 | 5.1 | 2.64 | 8.1 | 0 | 0 | 1.7 | 19.8 | 8.3 | | | |
| 16B | 527 | 70 | A | 0.5 | 5.1 | 2.64 | 15.3 | 16.3 | 31.33 | 16.2 | 11.7 | 16.7 | 3.1 | 14.9 | 6.9 |
| 16C | 527 | 70 | B | 0.5 | 2.33 | 1.2 | 28.3 | 32.8 | 46.6 | 15.9 | 6.3 | 18.6 | 2.2 | 12.9 | 11.6 |
| 17A | 511 | 51 | B | 0.5 | 11 | 6.4 | 17.2 | 28 | 45.2 | 8.2 | 11.8 | 20.5 | 1.1 | 11.3 | 11.3 |
| 17B | 522 | 51 | B | 0.5 | 11 | 6.4 | 19.7 | 30.4 | 47.8 | 8.2 | 11.9 | 20.2 | .7 | 19.1 | 12.5 |
| 22A | 504 | 50 | B | 0.5 | 12 | 6.1 | 8 | | | | | | | | |
| 22B | 504 | 308 | B | 0.5 | 5.4 | 2.8 | 14.3 | 15 | 33.5 | 5.8 | 11.7 | 22.6 | 2.1 | 20.3 | 8 |
| 19 | 542 | 300 | 2F | 0.1 | 4.65 | 3.14 | 70.8 | 12.7 | 17.9 | 26.7 | 3.7 | 28.3 | 3.9 | 20.6 | 8.6 |
| 20 | 532 | 300 | 2D | 0.1 | 4.65 | 3.01 | 55.6 | 16.1 | 27.4 | 20.1 | 3.5 | 19.9 | 5.3 | 25 | 5.2 |
| 21 | 520 | 300 | 2D | 0.1 | 5.01 | 3.25 | 41.6 | 15 | 30.8 | 11.5 | 12.3 | 21.8 | 3.1 | 32.4 | 3.2 |
| 23 | 560 | 305 | 2E | 0.1 | 4.65 | 3.52 | 100 | 0 | 0 | 100 | | | | | |

In carrying out the invention, the discharge from the reaction zone is withdrawn separately as gaseous and liquid effluents. As noted previously, the liquid effluent, is highly aromatic and typically contains 95 wt. % or more aromatic compounds. This higher aromatic content of the liquid effluent is particularly advantageous in that it permits rapid separation of the nonaromatic components by conventional distillation procedures rather than the solvent extraction processes normally required for the separation of aliphatic and cycloaliphatic compounds from aromatic product streams.

In view of the limitation imposed upon the conversion of the paraffinic hydrocarbons to olefins it is particularly advantageous in the present invention to separate the $C_2$–$C_5$ hydrocarbons from both the liquid and gaseous effluents and to recycle these compounds to the reaction zone. Preferably, the stock recycled to the reaction zone is composed predominantly of $C_3$–$C_5$ hydrocarbons.

Turning now to the drawing, there is illustrated a simplified flow diagram of a conversion process carried out in accordance with the present invention. Where the paraffinic feedstream has an unacceptably high water content, it is applied first to a dessicant zone 2 where substantial dehydration of the feedstream occurs. The zone may contain any suitable hydroscopic material such as potassium hydroxide. Preferably the water content of the feedstream is reduced to a value of about 20 ppm or less. The output from the dessicant zone as applied to reaction zone 4 which is operated at the conversion conditions described previously and is provided with one or more catalyst beds containing a catalyst system in accordance with the present invention. A plurality of catalysts beds may be employed with reheating facilities between successive beds. That is, as the flow stream is withdrawn from one bed, it is reheated to the desired operating temperature, i.e., 500° C. or above prior to being passed to the next catalyst bed. The reaction zone may be of the fixed bed or moving bed type, as will be understood by those skilled in the art. As a practical matter, the reaction zone may comprise a plurality of reaction vessels to allow for catalyst regeneration without interrupting the conversion process.

The gaseous and liquid effluent streams from the reaction zone 4 are applied to fractionating units 5 and 6, respectively. In unit 5, the $C_2$–$C_5$ hydrocarbons are separated from methane and inorganic gases (carbon monoxide, carbon dioxide and hydrogen) and withdrawn via line 8. The overheads from the fractionation unit 6 comprises $C_2$–$C_5$ hydrocarbons and are mixed with the bottoms from unit 5 for recycling to the inlet side of the dehydration unit 2. The substantially pure aromatic product is withdrawn from the bottom of unit 6 via line 10.

Having described specific embodiments of the present invention, it will be understood that modifications thereof may be suggested to those skilled in the art, and it is intended to cover all such modifications as fall within the scope of the appended claims.

We claim:

1. In a method of producing aromatic compounds from a paraffin containing feed stock, the combination comprising:
   (a) passing said feedstock into a reaction zone into contact with a catalyst system within said reaction zone comprising a discrete physical mixture of a shape-selective crystalline silica polymorph silicalite homologation catalyst and a metal or metal oxide dehydrogenation catalyst,
   (b) providing a temperature within said reaction zone sufficient to cause the dehydrogenation of paraffinic hydrocarbons to olefins, the oligomerization of olefinic hydrocarbons to cyclic naphthenes and the aromatization of said naphthenes, and
   (c) providing temperature and pressure conditions and relative concentrations of said silicalite catalyst and said dehydrogenation catalyst in said mixture to provide a relationship between the thermodynamic constraint for the dehydrogenation of said paraffinic hydrocarbons and the balancing of the kinetics of said dehydrogenation and oligomerization reactions to limit the olefin concentration within said reaction zone to a value which does not produce substantial coking of said catalyst system.

2. The method of claim 1 wherein said feedstock is predominantly paraffinic.

3. The method of claim 1 wherein the rate constant for said oligomerization reaction is at least as great as the rate constant for said dehydrogenation reaction.

4. The method of claim 3 wheren the rate constant for said oligomerization is less than the rate constant for said aromatization reaction.

5. The method of claim 1 wherein the rate constant for said oligomerization reaction is greater than the rate constant for said dehydrogenation reaction, thereby limiting the olefin concentration to value less than the equilibrium olefin concentration at the pressure and temperature of said reaction zone.

6. The method of claim 1 wherein the temperature within said reaction zone is at least 500° C.

7. The method of claim 6 wherein the pressure within said reaction zone is at least 2 bars.

8. The method of claim 1 wherein the temperature within said reaction zone is within the range of 500°–600° C. and the pressure within said reaction zone is within the range of 2–21 bars.

9. The method of claim 1 further comprised the steps of separately withdrawing gaseous and liquid effluents from said reaction zone, separating $C_2$–$C_5$ hydrocarbons from each of said gaseous and liquid effluents, and recycling said $C_2$–$C_5$ hydrocarbons to said reaction zone.

10. The method of claim 1 wherein said catalyst system is in a particulate form comprising pellets formed of crystallites of said dehydrogenation catalyst and said silicalite.

11. The method of claim 10 wherein said pellets have an average particle size within the range of about 1–4 millimeters.

12. The method of claim 1 wherein said catalyst system is in a particulate form comprising granules of said silicalite and granules of said dehydrogenation catalyst mixed together to provide said discrete physical mixture.

13. The method of claim 12 wherein each of said silicalite and said dehydrogenation catalyst have an average particle size within the range of about 0.2–4 millimeters.

14. The method of claim 1 wherein said dehydrogenation catalyst is zinc oxide.

15. The method of claim 14 wherein the weight ratio of zinc oxide to silicalite in said mixture is within the range of 0.1–1.

16. The method of claim 15 wherein the weight ratio of zinc oxide to silicalite in said mixture is within the range of 0.3–0.5.

17. The method of claim 14 wherein the temperature of said reaction zone is within the range of 500°–600° C.

18. The method of claim 17 wherein the temperatuare within said reaction zone is within the range of 520°–550° C.

19. The method of claim 1 further comprising this step of interrupting the flow of said feedstock to said reaction zone, and supplying a nitrogenated air feed to said reaction zone while maintaining said reaction zone at a temperature of within the range of 400°–500° C. to regenerate said catalysts.

20. The method of claim 9 wherein said recycle stock is comprised predominantly of $C_3$–$C_5$ hydrocarbons.

21. The method of claim 3 further comprising the steps of separately withdrawing gaseous and liquid effluents from said reaction zone, separating $C_2$–$C_5$ hydrocarbons from each of said gaseous and liquid effluents to arrive at a recycle stock comprised predominantly of $C_3$–$C_5$ hydrocarbons and recycling said hydrocarbons to said reaction zone.

* * * * *